(12) United States Patent
Guo et al.

(10) Patent No.: US 10,162,091 B1
(45) Date of Patent: Dec. 25, 2018

(54) SILICON FILM OPTICAL FILTERING SYSTEMS AND METHODS OF FABRICATION

(71) Applicants: Junpeng Guo, Madison, AL (US); Seyed Sadreddin Mirshafieyan, Huntsville, AL (US)

(72) Inventors: Junpeng Guo, Madison, AL (US); Seyed Sadreddin Mirshafieyan, Huntsville, AL (US)

(73) Assignee: Board of Trustees of the University of Alabama, for and on behalf of the University of Alabama in Huntsville, Huntsville, AL (US)

( * ) Notice: Subject to any disclaimer, the term of this patent is extended or adjusted under 35 U.S.C. 154(b) by 124 days.

(21) Appl. No.: 14/885,843

(22) Filed: Oct. 16, 2015

(51) Int. Cl.
  *G02B 5/28* (2006.01)
  *G01J 3/42* (2006.01)

(52) U.S. Cl.
  CPC ............... *G02B 5/286* (2013.01); *G01J 3/42* (2013.01); *G02B 5/288* (2013.01)

(58) Field of Classification Search
  CPC ............ G02B 5/22; G02B 5/265; G02B 5/26
  USPC ............... 359/885, 359, 360, 589, 586–588
  See application file for complete search history.

(56) References Cited

U.S. PATENT DOCUMENTS

| | | | | |
|---|---|---|---|---|
| 3,721,584 A | * | 3/1973 | Diem | ............... C23C 16/24 257/E21.266 |
| 6,108,064 A | * | 8/2000 | Minoura | ............. G02F 1/13363 349/113 |
| 7,106,922 B2 | | 9/2006 | Liu | |
| 7,212,342 B2 | * | 5/2007 | Lan | ............... G02F 1/133512 359/585 |
| 7,901,870 B1 | | 3/2011 | Wach | |
| 8,749,903 B2 | | 6/2014 | Yamada | |
| 9,354,369 B2 | | 5/2016 | Hendrix et al. | |
| 2013/0265668 A1 | * | 10/2013 | Banerjee | ............... G02B 5/22 359/885 |

OTHER PUBLICATIONS

Guo, et al., U.S. Appl. No. 15/404,000, entitled, "Omni-Directional Ultra-Thin Reflection Optical Filters and Methods of Fabrication," filed Jan. 11, 2017.
World News, "Thin-Film Filters," Laser Focus World, www.laserfocusworld.com, p. 24, Jan. 2015.
Lipson, et al., "Low Loss Tunable Optical Filter Using Silicon Photonic Band Gap Mirrors," Proc. Transducers 2007, pp. 1445-1448, Jun. 10-14, 2007.

* cited by examiner

*Primary Examiner* — Thanh Luu
(74) *Attorney, Agent, or Firm* — Maynard Cooper & Gale, P.C.; Jon E. Holland

(57) ABSTRACT

An optical filter has a layer of silicon film deposited onto a metallic substrate surface at a silicon film thickness corresponding to a wavelength of light to be filtered from incoming light. The critical coupling of light to the optical cavity formed by the silicon film on metal surface results in a strong and near perfect absorption of the light at a resonance wavelength and strong absorption in the wavelength region near the peak absorption wavelength. Other wavelengths of the incoming wave are reflected by the device so the spectral content of light is changed. By controlling the thickness of the silicon film and/or other factors, such as the extent to which the silicon film is annealed or the type of metal beneath the silicon film, the wavelength of the light absorbed by the silicon film can be precisely controlled.

21 Claims, 8 Drawing Sheets

SILICON FILM OPTICAL FILTERING SYSTEMS AND METHODS OF FABRICATION

STATEMENT REGARDING FEDERALLY SPONSORED RESEARCH OR DEVELOPMENT

This invention was made with Government support under EPS1158862 awarded by the National Science Foundation. The Government has certain rights in the invention.

RELATED ART

A variety of applications require devices that display color vibrantly and accurately in ambient light. It is often desirable for the wavelengths of light absorbed (and reflected) by a device to remain constant, even when viewed from a wide range of angles. Conventional optical filters capable of achieving this effect are often expensive and complex.

In conventional low-cost optical filters, distortion of the reflected wavelengths often varies with the angle of incidence. Thus, the desired color is accurately reflected only for a limited range of reflection angles. Improved low-cost optical filters capable of accurately reflecting a desired wavelength range across a wide range of angles are generally desired.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

Figure 1:
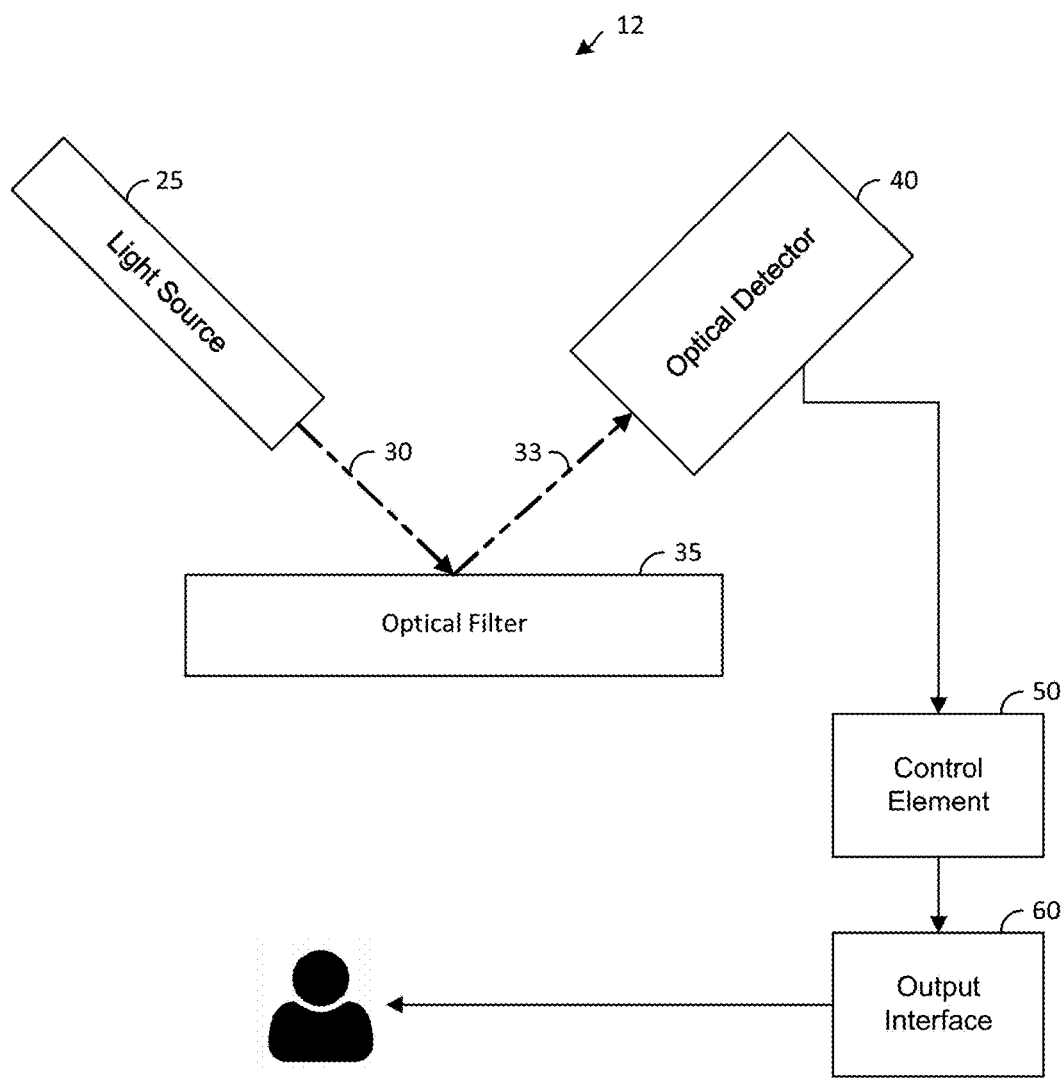
FIG. 1 depicts an exemplary embodiment of an optical filtering system.

The present disclosure generally pertains to optical filtering systems and methods. An optical filter in accordance with an exemplary embodiment has a layer of silicon film deposited onto a metallic substrate at a thickness corresponding to a wavelength of light to be filtered from incoming light. If desired, thermal annealing of the silicon film may be performed for precisely tuning the center of the absorption peak. During operation, a light source emits light toward the silicon film. The thickness of the silicon film is selected to achieve near perfect absorption of the incoming light into the silicon film at a particular wavelength. Other wavelengths of the incoming light are reflected by the silicon film such that the reflected light has an absorption peak centered about the particular wavelength, referred to hereafter as the "center wavelength." An optical detector detects the reflected light and generates a signal that is indicative of the light detected. A control element receives the signal from the optical detector and provides an output that is indicative of the light detected by the optical detector. The control element communicates the output to an output device, which displays the output to a user. By controlling the thickness of the silicon film and/or other factors, such as the extent to which the silicon film is annealed or the type of metal beneath the silicon film, the center wavelength of the light absorbed by the silicon film can be precisely controlled.

It has been observed that silicon film can be used to realize spectral-selective near perfect light absorption where critical coupling conditions occur to the second order optical resonance mode of a silicon film optical cavity. Silicon is a low cost material that is widely used in the electronics industry. Additionally, silicon has the smallest optical extinction coefficient among commonly used high-index semi-conductive materials in the range of visible light wavelengths. "Near perfect" absorption of light by an optical filter generally refers to spectrally selective absorption of incoming incident light where greater than 90% of the incoming incident light at the selected wavelength or wavelengths are absorbed. Experiments have shown that absorption rates close to 100% (e.g., greater than 98%) can be achieved through the use of silicon films, as described herein. In addition, the optical reflectance of the silicon film is angle-insensitive; this results in colors that remain unchanged when viewed from different angles, even at large angles of incidence with regard to the surface normal of the silicon film.

A single layer of silicon film on a metal surface can function as an optical cavity (e.g., an asymmetric Fabry-Perot) for achieving near perfect light absorption. The peak absorption wavelength can be altered by varying the silicon film's thickness. Increasing a silicon film's thickness allows for additional resonance modes to occur in the optical cavity. Importantly, it has been observed that near perfect light absorption occurs in the silicon-on-metal optical cavity at the critical coupling condition met by the second optical resonance mode. Light absorption occurs for other resonance modes, but not necessarily near perfect light absorption. Thus, the thickness of the silicon film is preferably sufficient to meet the critical coupling condition of the second optical resonance mode.

As noted above, the peak wavelength of light absorbed by the silicon thin-film on metal optical cavity can be altered (e.g., tuned) by varying the thickness of a silicon film. By increasing the silicon thickness, the peak absorption wavelength generally shifts to a longer wavelength. It has further been observed that the peak wavelength of light absorbed by silicon films can be shifted by subjecting the silicon films to thermal annealing. Thermal annealing (e.g., using a furnace) of the silicon film for a period of time changes a silicon film from an amorphous phase to a polycrystalline phase. It has been observed that shifting silicon's phase from amorphous to polycrystalline significantly reduces the imaginary part of the silicon film's refractive index. This results in a shift in wavelengths of light absorbed by the silicon thin-film toward a shorter wavelength (e.g., produces "blue-shifts" in the peak wavelength absorbed). The change of silicon from amorphous phase to polycrystalline or crystalline phase changes the silicon's refractive index.

Silicon and metal films can be deposited onto a metal surface using a variety of techniques. For example, amorphous silicon film and metal film may be deposited onto various surfaces using a sputter machine. Using this technique, thickness of the silicon film (and, thus, wavelength of light absorbed by it) can be controlled by varying sputtering time. In this regard, a single layer of silicon film can be deposited onto a variety of metal film surfaces. Silicon films can be deposited using a sputter onto soft, hard, curved, flat, smooth or rough substrates. Thus, optical filtering using silicon films is possible for a wide variety of applications. Since silicon is used to from the resonant cavity, the filter can be better resistant to higher temperatures. Indeed, the materials can be selected so that the filter is capable of withstanding temperatures up to about 500° C., which is much greater than chemical dyes.

Silicon films offer a robust alternative to traditional optical filters and coloring methods that are expensive and have use in limited applications. First, low cost and abundant supply of silicon makes it ideal for widespread use as an optical filter material. Traditional optical filters are expensive and burdensome to manufacture. Additionally, inherent properties of silicon give it an advantage over conventional coloring methods. For example, high temperature tolerance of silicon films (from about −250° Celsius (C) to about 500° C.) makes it an ideal alternative to conventional chemical dyes that are unable to withstand similarly high temperatures. Thus, use of silicon films as spectral-selective light absorbers allows for use in a variety of applications, such as low cost optical filters, enhanced photodetectors, solar cells and colorimetric biochemical sensors.

FIG. 1 depicts an exemplary embodiment of an optical filtering system 12. The system 12 has a light source 25 for generating and outputting light 30 and an optical filter 35 for filtering incident light from the light source 25 by absorbing at least one wavelength of the light 30. Light not absorbed by the optical filter 35 is reflected as reflected light 37. This light 37 reflected by the optical filter 35 is detected by an optical detector 40. The optical detector 40 communicates a signal to a control element 50 that generates an output (e.g., a message, data, or image) indicative of the reflected light 37 detected by the optical detector 40. The control element 50 then communicates the output to an output interface 60, which displays or otherwise renders the output. As an example, the output may define a message that specifies or otherwise indicates the wavelength at the center of the absorption peak in the reflected light 37. In another example, the output may define an image captured by the optical detector 40.

In an exemplary embodiment, the light source 25 of the system 12 is configured to emit light and comprises an unpolarized broadband halogen light source. That is, light 30 generated by the light source 25 is unpolarized. Other light sources 25 are possible in other embodiments. Note that the light source 25 shown by FIG. 1 emits light 30 in at least the visible spectral range of wavelengths. In other embodiments, the light source 25 may be configured to emit light 30 in other spectral ranges (e.g., infrared and ultraviolet spectral ranges).

Note that the use of a light source 24 and an optical detector 40 is unnecessary. For example, the optical filter 35 may filter ambient light that is incident on the surface of the filter 35, which changes the color of the reflected light for observation by a human. Thus, the optical filter 35 may be positioned on the surface of an object in order to change the color of the object perceived by a human. Other uses of the filter 35 are possible in other embodiments.

The optical filter 35 shown by FIG. 1 is configured to absorb at least one wavelength of the light 30. The optical filter 35 has a silicon thin-film (not specifically shown in FIG. 1) positioned on its surface and exposed to incident light 30 emitted by the light source 25, as discussed at length below. As the light 30 becomes incident on the silicon thin-film surface (not specifically shown in FIG. 1) of the optical filter 35, light of at least one wavelength is absorbed by the silicon thin-film structure. The light that is not absorbed is instead reflected by the optical filter 35 (e.g., the silicon thin-film surface, not specifically shown in FIG. 1) as reflected light 37. Note that the reflected light 37 shown in FIG. 1 does not include all of the wavelengths found in the light 30 because the optical filter 35 has absorbed at least one peak wavelength. In this regard, the reflected light 37 has an absorption peak centered about a specific wavelength, referred to as the "center wavelength" of the absorption peak.

FIG. 1 further depicts an optical detector 40 for generally detecting reflected light 37. In one embodiment, the optical detector 40 comprises an optoelectronic sensor, but other devices suitable for detecting light as required herein are possible in other embodiments. A single optical detector 40 is shown by FIG. 1, but the system 12 may comprise any number of optical detectors 40 in other embodiments.

The optical detector 40 is coupled to a control element 50. In an exemplary embodiment, the control element 50 communicates with and generally controls the functions of the optical detector 40. The control element 50 may be implemented in hardware or a combination of hardware and software. In some embodiments, the control element 50 may comprise software running on an instruction execution apparatus, such as a digital signal processor (DSP) or central processing unit (CPU). In such embodiment, the software may be stored in memory (not shown). Note that the control element 50 and optical detector 40 may comprise wireless communication interfaces (not specifically shown) for communicating wirelessly with one another. Alternatively, the control element 50 and the optical detector 40 may be coupled to one another via one or more physical connections (e.g., electrical or optical) for permitting communication between the control element 50 and the optical detector 40.

The optical detector 40 is configured to generate a signal that is indicative of light detected by the optical detector 40 and communicate the signal to the control element 50. In one embodiment, the control element 50 is configured to receive a signal from the optical detector 40 and calculate or otherwise determine a parameter indicative of the light detected by the optical detector 40. As an example, the control element 50 may determine the center wavelength of an absorption peak in the light or the boundary wavelengths of such absorption peak. Alternatively, the control element may determine the color of the detected light or capture an image of the detected light. As shown by FIG. 1, the control element 50 is coupled to an output interface 60 that is configured display information indicative of the parameter or the color(s) determined by the control element 50. As an example, the display may include data indicating which wavelength(s) have been absorbed or the colors of light that are detected, or the display may define an image captured by the optical detector 40.

In the exemplary embodiment shown by FIG. 1, the angle of incidence for the light 30 emitted by the light source 25 as shown by FIG. 1 is approximately 30° from the surface normal of the silicon film 35, although other angles in other embodiments are possible. Near perfect light absorption by the optical filter 35 results in consistent light reflection across a wide range of viewing angles. That is, the color of light reflected by the optical filter is angle-insensitive for a large range of angles. In this regard, it has been observed that the wavelength of reflected light 33 detected by the optical detector 40 will remain substantially constant at angles of incidence of up to 60° or more with respect to a line normal to the surface of the optical filter 35. Thus, the optical filter 35 appears to maintain approximately the same color when viewed at angles that otherwise may result in distortion of reflected wavelengths in conventional optical filters.

Figure 2A:
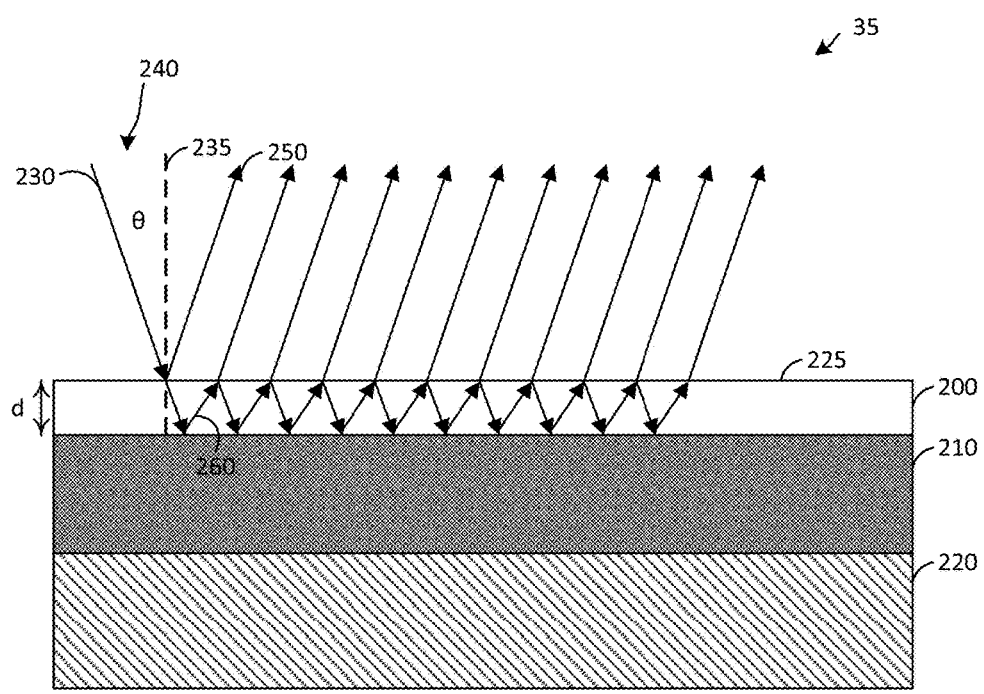
FIG. 2A is a cross sectional view depicting an exemplary embodiment of an optical filter, such as is depicted by FIG. 1.

FIG. 2A is a cross sectional view depicting an exemplary embodiment of an optical filter 35. As shown by FIG. 2A, the optical filter 35 has a thin film 200 that is deposited on a surface of an opaque metal substrate 210. In an exemplary embodiment, the thin film 200 is composed of silicon-based material, such as pure silicon or a combination of silicon and other elements, and the substrate 210 is composed of a metal, such as aluminum. The aluminum metal layer is thick enough to block the light transmission through it. Unless otherwise indicated, it will be assumed hereafter that the silicon thin film 200 is composed of pure silicon and that the substrate 210 is composed of aluminum, but it should be emphasized that other types of materials or combinations of materials are possible in other embodiments.

In an exemplary embodiment, the silicon thin-film 200 has a thickness between about 110 nm and 140 nm, though other thicknesses of the silicon thin-film 200 are possible in other embodiments. In the instant embodiment, the aluminum substrate 210 has a thickness of about 300 nm, although other thicknesses are possible, and is deposited onto a substrate 220. In one embodiment, the substrate 220 is composed of glass, and the thickness of the substrate 220 is about 4 inches. However, other types of materials and thicknesses are possible in other embodiments. Note that the aluminum substrate 210 is thick enough to block light transmission (i.e., light is reflected). Additionally, as noted hereinabove, the silicon thin-film 200 may be deposited on a surface of other materials, and it is not necessary for the optical filter 35 to comprise an aluminum substrate 210 and glass substrate 220 in other embodiments.

An upper face 225 of the silicon thin-film 200 is exposed to light, such as light emitted by the light source 25 of FIG. 1. In the exemplary embodiment shown by FIG. 2A, an incident light wave 230 makes contact with the surface 225. In the context of this document, the angle at which an incident light 230 makes contact with a surface 225 relative to a line 235 normal to such surface is referred to as an angle of incidence 240. That is, the angle of incidence 240 is the angle formed between the direction of propagation of the incident light wave 230 and a line 235 that is normal to the surface 225 of the optical filter 35.

FIG. 2A further depicts reflected light 250. The reflected light 250 depicted by FIG. 2A has been reflected by the surface 225 of the silicon thin-film 200 or exits the silicon thin-film 225 after reflecting from the layer 210. Note that less than all of the light is reflected by the surface 225. In this regard, light at a certain wavelength corresponding to the thickness of the silicon thin-film 200 is absorbed into the filter 35. Specifically, the absorbed light 260 propagates through the silicon thin-film 200 and reflects off of the surface of the aluminum substrate 210. As shown by FIG. 2A, the absorbed light 260 continues to reflect between the upper surface of the substrate 210 and the upper surface of the silicon thin-film 200 until the energy of the absorbed light 260 is dissipated. Note that at each reflection point, a very small portion of the light 260 may escape from the silicon thin-film (e.g., absorb into the aluminum substrate 210 for a lower reflection point or pass through the upper surface of the silicon thin-film 200 into the surrounding environment (e.g., air) for an upper reflection point).

The propagation of light through the silicon thin-film 200 produces standing waves in the silicon thin-film for certain resonant frequencies. The standing wave patterns produced are generally referred to as "modes." The resonance enhances optical interference at wavelengths corresponding to the resonant frequencies, thereby causing the silicon thin-film 200 to absorb a greater amount of light at such wavelengths. Near perfect absorption is achieved for the wavelength corresponding to the second order optical resonance mode of the film 200, which is based on the thickness d of the film 200, as well as other factors such as the extent to which the film 200 has been annealed. Thus, the reflected light 250 includes an absorption peak centered about the foregoing wavelength, referred to as the "center wavelength" of the absorption peak.

As shown by FIG. 2A, no light from the incident light 230 passes completely through the aluminum substrate 210, though it is possible for light to pass completely through the substrate 210 in other embodiments. The peak wavelength of light absorbed varies as a function of the thickness d of the silicon thin-film 200, which in turn alters the optical resonance modes that occur within the thin film 200. As noted above, near perfect optical absorption in the visible optical spectrum range occurs via the critical coupling condition when the thin film 200 is thick enough to accommodate second mode optical resonance. In one embodiment, the silicon thin-film 200 has a thickness between about 110 nm and 140 nm, but other thicknesses of the silicon thin-film 200 are possible in other embodiments. Varying the thickness of the silicon thin-film 200 within such range causes the absorption peak to shift such that the wavelength at the absorption peak can be controlled by controlling the thickness of the silicon thin-film 200. Note that an absorption peak may also be shifted by annealing the silicon thin-film 200. Thus, the absorption peak wavelength may be tuned through selection of the thickness of the silicon thin-film 200 and annealing of the silicon thin-film 200 as may be desired. Further, as will be described in more detail below, light may slightly penetrate the surface of the metal substrate 210, thereby increasing the distance that the light penetrates the filter 35 and altering the optical resonance wavelength within the silicon thin-film cavity. Thus, tuning of the absorption peak may also be achieved through selection of the material for the metal film 210.

Figure 2B:
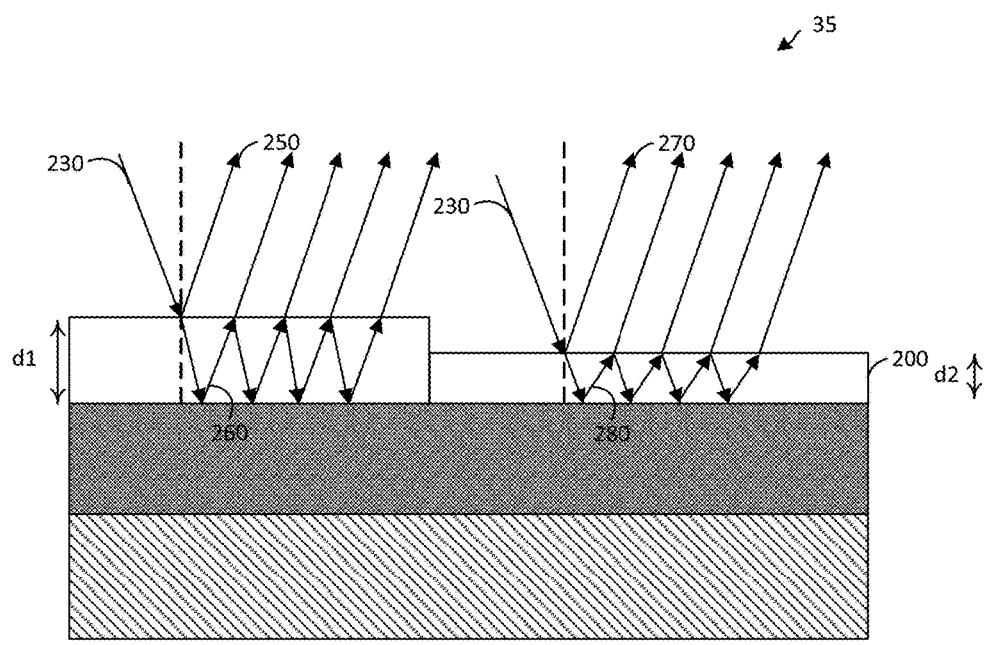
FIG. 2B is a cross sectional view depicting an exemplary embodiment of an optical filter, such as is depicted by FIG. 1.

FIG. 2B is a cross-sectional view depicting an exemplary embodiment of an optical filter 35. In some embodiments, the thickness of the silicon thin-film 200 may be varied across the width of the filter 35 for creating multiple absorption peaks, and thus, reflecting any desired set of wavelengths. In the embodiment shown by FIG. 2B, the silicon thin-film 200 has thicknesses d1 and d2, where d1 is not equal to d2, and both d1 and d2 are sufficiently large to achieve the critical coupling condition of the optical resonance mode for incident light 230. As incident light 230 makes contact with the optical filter 35, the portion of the optical filter 35 having a silicon thin-film 200 of thickness d1 absorbs light 260 with an absorption peak at a first wavelength. Concurrently, the portion of the optical filter 35 having a silicon thin-film 200 of thickness d2 absorbs light 280 with an absorption peak at second wavelength different than the first wavelength. Thus, light reflecting from the surface of the portion of the silicon thin-film 200 having a thickness d1 may exhibit a different color than light reflecting from the surface of the portion of the silicon thin-film 200 having a thickness d2. Thus, the silicon thin-film 200 may be patterned with different thicknesses to define a desired image where any portion of the surface of the silicon thin-film may exhibit a different color relative to any other portion. Any silicon thin-film may be divided into any number of different portions having different thicknesses in order to define any desired pattern for the image reflected by the silicon thin-film 200. Thus, the optical filter can be configured to achieve near perfect absorption of any set of wavelengths such that the spectrum of the reflected light can be tailored as may be desired to achieve a certain overall color.

Note that varying the thickness of silicon thin-film 200 across the filter may be achieved by varying sputtering time when the silicon thin-film 200 is deposited or by etching of the silicon thin-film 200 after it has been deposited onto the substrate 210. In this regard, it is possible to create color patterns by varying the thickness (e.g., by having different thicknesses of the film 200 on different portions of the surface of optical filter 35) of the silicon thin-film 200 that is deposited on the surface of the aluminum substrate 210. Note also that the silicon thin-film 200 shown by FIGS. 2A and 2B may be thermally annealed to shift any absorption peak, but it is not necessary to perform thermal annealing on the silicon thin-film 200 in all embodiments.

In addition, as described above, it is possible to tune the absorption peak in the reflected light 250 through annealing. Thus, it is possible to create a pattern in the surface of the silicon thin-film, as described above with reference to FIG. 2B, by annealing different portions of the silicon thin-film differently rather than changing the thicknesses of the two portions. By annealing one portion of the silicon thin-film 200 differently than another portion, the light reflected by each portion may have a different color. If desired, a combination of controlling the thicknesses of different portions of the silicon thin-film 200 differently and annealing different portions of the silicon thin-film differently may be performed in order to define any type of image on the surface of the silicon thin-film 200 as may be desired.

Figures 3A, 3B:
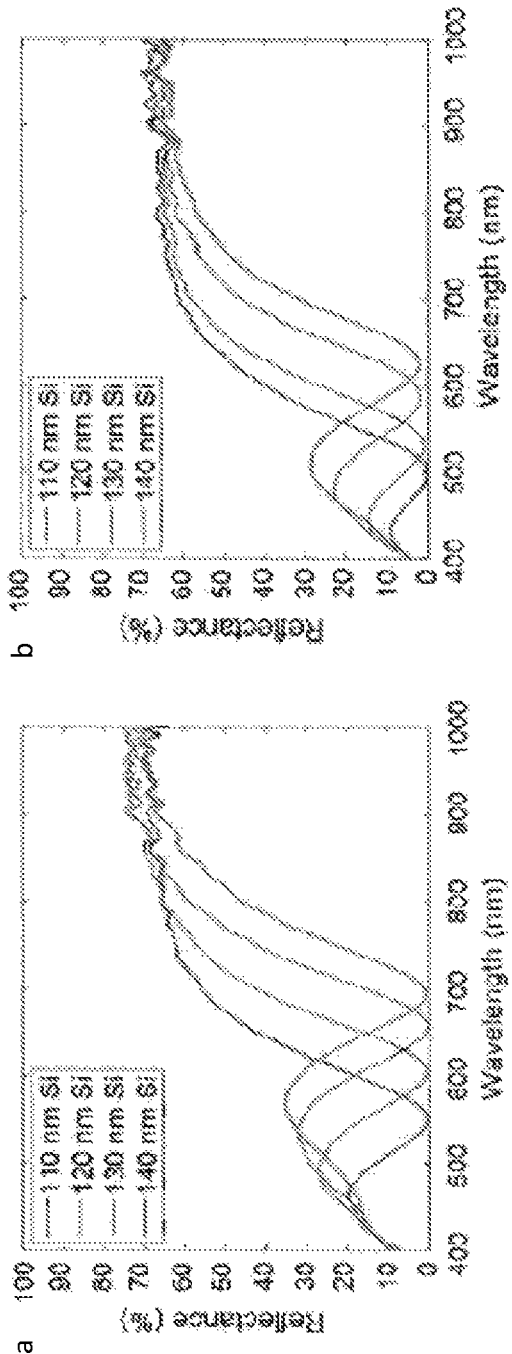
FIG. 3A is a plot illustrating exemplary measurements of reflectance of light at a variety of wavelengths by optical filters having silicon films of varying thicknesses.
FIG. 3B is a plot illustrating exemplary measurements of reflectance of light at a variety of wavelengths by optical filters having thermally annealed silicon films of varying thicknesses.

FIG. 3 depicts a plot illustrating exemplary measurements of absorption occurring at various wavelengths for silicon thin-film. The exemplary measurements of FIG. 3 include measurements for silicon films of thicknesses 110 nm, 120 nm, 130 nm, and 140 nm. As shown by FIG. 3A, critical coupling resulting in near perfect optical absorption (e.g., zero reflectance) occurs for each thickness of silicon film listed. Note that critical coupling condition is a condition in which the optical power coupled when light becomes incident on the surface of the silicon thin-film equals the optical loss per resonance cycle in the optical cavity (here, the silicon thin-film). The second order resonance mode of the thin film optical cavity can meet this critical coupling condition because of increased silicon film thickness. The second order optical resonance mode appears in a visible spectral range when the silicon thin-film thickness increases above 90 nm. As depicted by FIG. 3, at the second order optical resonance mode for silicon film thicknesses from 110 nm to 140 nm, critical coupling conditions can be met and near perfect light absorption occurs in the optical wavelength ranges from about 552 nm to about 700 nm. Note that the absorption wavelengths for the exemplary measurements shown by FIG. 3A are approximately 552 nm, 605 nm, 657 nm, and 700 nm for silicon thin-films with thicknesses of approximately 110 nm, 120 nm, 130 nm, and 140 nm, respectively. As demonstrated by the exemplary measurements of FIG. 3A more than approximately 99% optical absorption occurs within a spectral reflective optical filter using silicon thin-film at the second order optical resonance wavelengths in the silicon thin-film's amorphous state. Note also that first and third order optical resonance modes do not likely result in complete absorption in the thin-film cavity because the critical condition is not likely met.

FIG. 3B depicts a plot showing exemplary measurements of optical reflectance following thermal annealing of a silicon thin-film at thicknesses of approximately 110 nm, 120 nm, 130 nm, and 140 nm. As also depicted by FIG. 3A, exemplary measurements of FIG. 3B reflect near perfect optical absorption for a variety of wavelengths. However, for silicon thin-films with thicknesses of approximately 110 nm, 120 nm, 130 nm, 140 nm, the exemplary measurements of FIG. 3B demonstrate absorption wavelengths exhibiting "blue shifts". This results in absorption at peak wavelengths of about 500 nm, 531 nm, 587 nm, and 625 nm respectively. For the thicknesses ranging between approximately 110 nm 140 nm, optical absorption in annealed silicon films exceeds about 98%.

Figure 4:
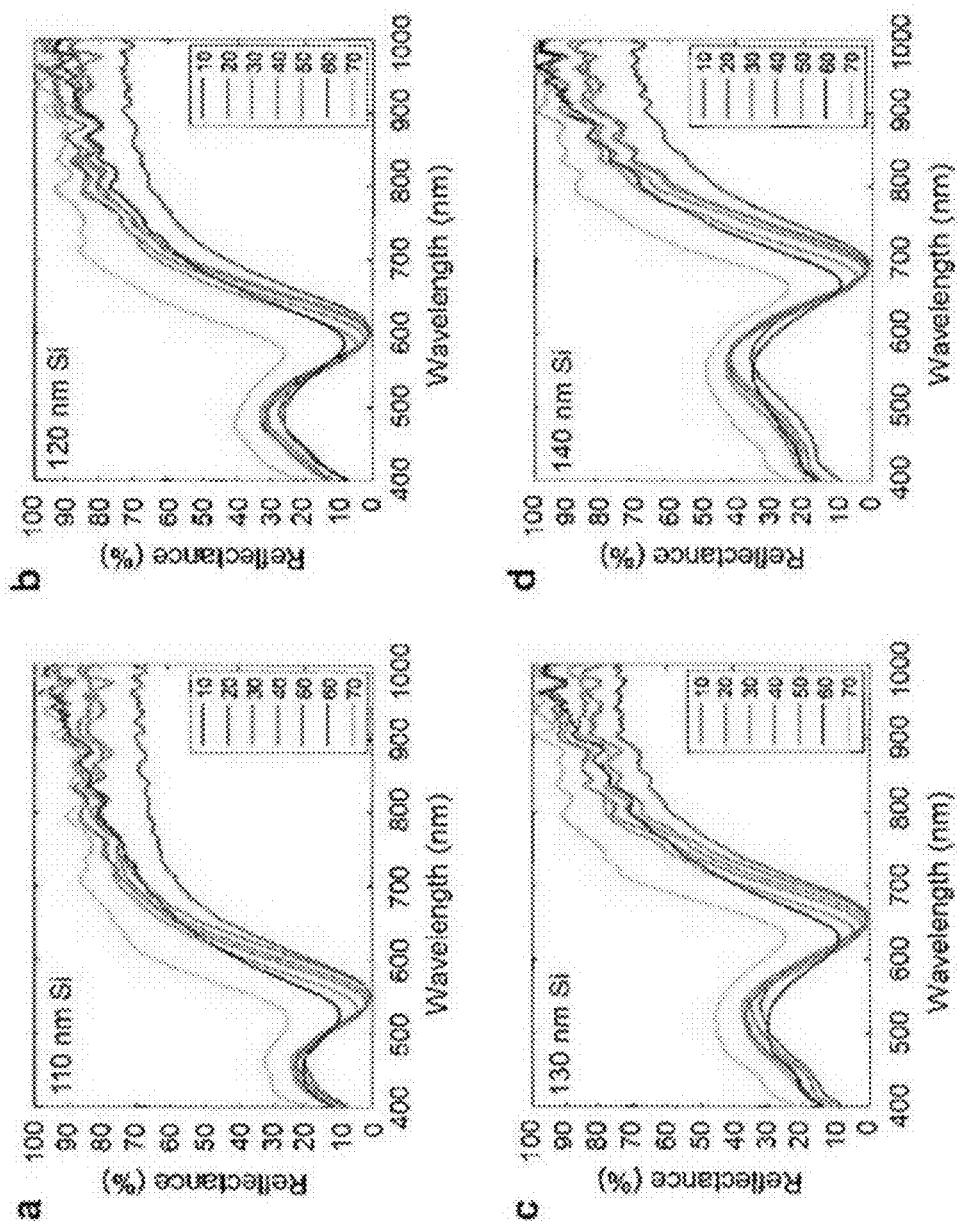
FIG. 4 depicts plots illustrating exemplary measurements of reflectance of light with incrementally-increasing incidence angles at a variety of wavelengths by an optical filter with a silicon thin-film having a thickness between about 110 nanometers and 140 nanometers.

FIG. 4 depicts a series of plots of exemplary measurements of reflectance of varying thicknesses of silicon thin-films when viewed at angles incremented by 10°. As noted above, use of silicon thin-films as an optical filter results in reflectance of light that is angle-insensitive across a wide a range of angles. FIG. 4 demonstrates that the wavelength at which peak absorption occurs in the silicon thin-film shifts to slightly shorter wavelengths as the angle of incidence increases. Likewise, the reflection peak wavelength does not exhibit distortion as the incident angle increases to 60°. In this regard, the exemplary measurements of FIG. 4 illustrate that peak wavelengths absorbed by the silicon thin-film remain constant, so that the color of the silicon thin film remains essentially unchanged, even when viewed from varying angles relative to the surface normal of the silicon thin-film.

Figure 5:
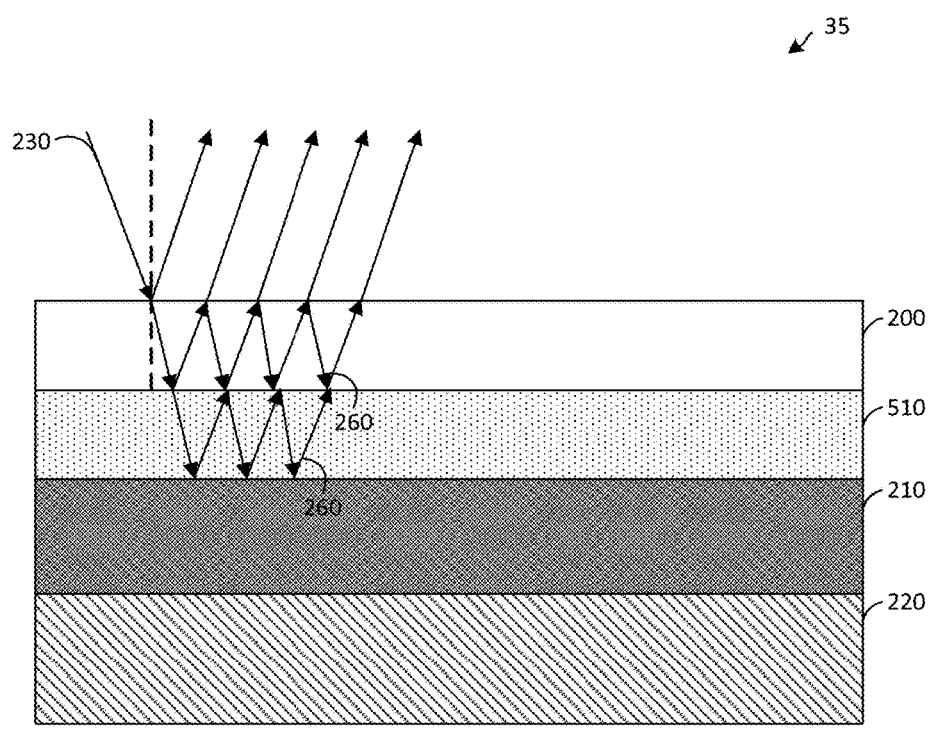
FIG. 5 is a cross sectional view depicting an exemplary embodiment of an optical filter having a layer comprising a dielectric film.

FIG. 5 depicts a cross sectional view of an exemplary embodiment of an optical filter 35 that is the same as the filter 35 shown by FIG. 2A except that the filter 35 of FIG. 5 has an additional layer 510 between the silicon thin-film 200 and the metal substrate 210. In one embodiment, the layer 510 is composed of a dielectric material, but other types of materials are possible in other embodiments. The addition of a transparent dielectric layer 510 between a layer of a silicon thin-film 200 and opaque metal layer 210 can achieve a narrower absorption peak than can be achieved by use of a silicon thin film 200 alone. That is, the spectral width of the absorption peak is reduced by the presence of the dielectric layer 510. In this regard, the dielectric layer 510 has a lower absorption loss coefficient in visible light frequencies than does the layer of silicon thin-film 200. This permits the absorbed light 260 to reflect back and forth between the silicon thin-film 200 and the substrate 210 longer (i.e., a greater number of times), thereby enhancing the optical interference occurring in the silicon thin-film. Thus, near perfect absorption can be achieved with a narrower absorption peak in the reflected light 250.

As noted above, the peak absorption wavelength may be tuned by altering the thickness of the silicon thin-film 200 or by annealing. As also described above, it has also been observed that the peak absorption wavelength of the optical filter 35 may be tuned through selection of the material of the metal substrate 210. Thus, it is possible to divide the substrate 210 into different types of metal materials in order to control a pattern of the image reflected off of the surface of the silicon thin-film 200, similar to the pattern described above for FIG. 2B. In this regard, by forming one portion of the silicon thin-film 200 on a metal different than the metal on which another portion of the silicon thin-film 200 is formed, the light reflected by each portion may have a different color. Thus, the colors reflected by the surface of the silicon thin-film 200 can be controlled across the face of the thin-film 200 without altering the thickness of the film 200 or annealing the film 200. If desired, a combination of controlling the thicknesses of portions of the silicon thin-film 200 differently, annealing portions of the silicon thin-film 200 differently, and/or forming portions of the silicon thin-film 200 on different types of materials (e.g., different metals) may be performed in order to define any type of image on the surface of the silicon thin-film 200 as may be desired.

Figure 6:
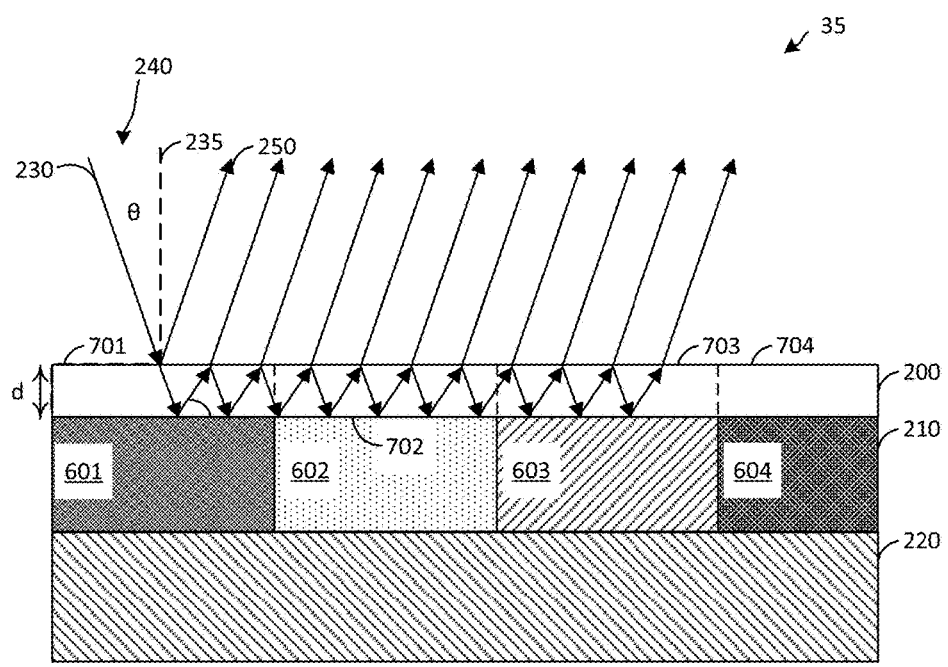
FIG. 6 is a cross sectional view depicting an exemplary embodiment of an optical filter having a layer comprising a plurality of opaque metals.

FIG. 6 depicts an exemplary embodiment of an optical filter 35 in which the substrate 210 is segmented into different types of metals. Specifically, the substrate 210 comprises portions 601-604 where each portion 601-604 is composed of a different type of metal. As described above, the absorbed light 260 propagating through the silicon thin-film 200 penetrates a small distance into the portions 601-604. Since each portion 601-604 is composed of a different material, the distance that the light penetrates each respective portion 601-604 is slightly different. Thus, a portion 701 of the silicon thin-film 200 formed on the substrate portion 601 will have different resonance wavelengths than the film portions 702-704 formed on the substrate portions 602-604 respectively. Thus, the absorption peak wavelength in the light reflected from portion 701 will be different from the absorption peak wavelengths in the light reflected from the other portions 702-704 such that the light reflected from the portion 701 will have a different color relative to the light reflected by the other portions 702-704. Similarly, the light reflected from each respective portion 702-704 will have a different color relative to the light reflected by the other portions of the silicon thin-film 200. Thus, by patterning the substrate 210 with different metal materials, any desired image may be reflected from the surface of the silicon thin-film 200. In the example shown by FIG. 6, four portions 601-604 are depicted, but the substrate 210 can be configured to have any number of portions 601-604 reflecting different colors of light in other embodiments.

Figure 7:
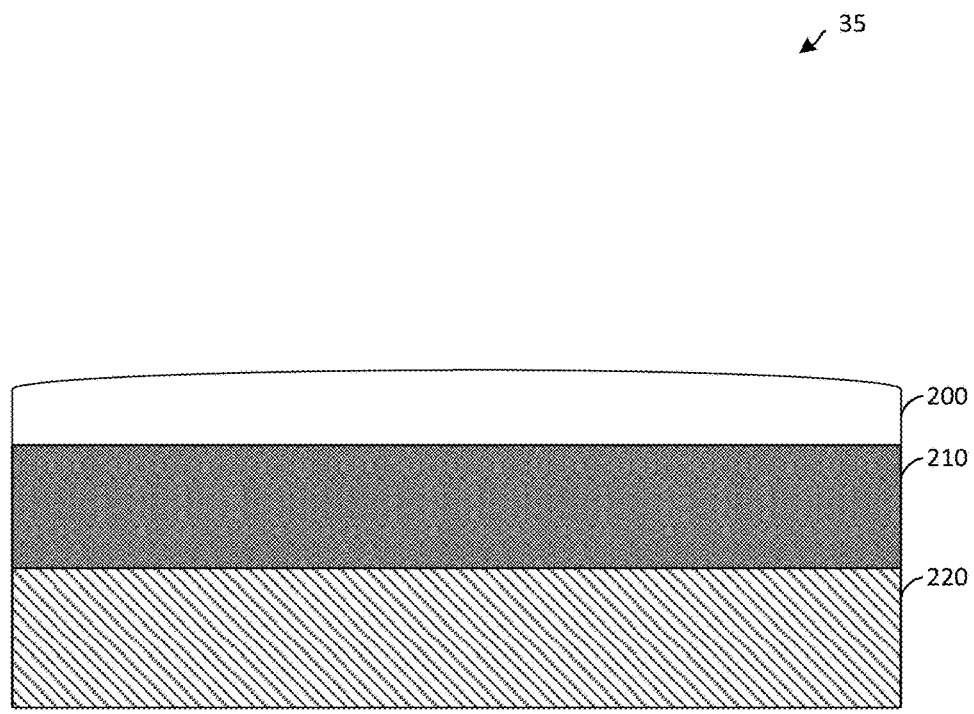
FIG. 7 is a cross sectional view depicting an exemplary embodiment of an optical filter having a curved surface.

Note that the dielectric film 200 shown by FIG. 2A and FIG. 6 has a generally flat surface profile, but other profiles of the film 200 are possible. In one embodiment, the film 200 has a curved surface profile, such as is depicted by FIG. 7. In this regard, the thickness of the film 200 varies across a width of the filter 35 to define a curvature on the surface of the film 200. Thus, across the curvature, the absorption peak at one point of the surface is different than at a different point such that different colors are exhibited by the light reflecting from the two points. Therefore, the resulting thickness variations produces a variation of colors reflected by the optical filter 35 across the surface of the silicon thin-film 200, as described above. Note that it is possible for a portion of the silicon thin-film to be flat and for other portions of the silicon thin-film to be non-flat, as may be desired.

In various embodiments described above, the layer 200 is described as a silicon thin-film. However, as noted above, other types of layers 200 are possible. As an example, it is possible for the layer 200 to be composed of other high refractive index semiconductor or lossy dielectric materials and for the substrate 210 to be composed of other metals such as titanium, chromium, copper, silver, and etc. The techniques of controlling the color of light reflected by the filter 35 by controlling the thickness of the layer 200, annealing the layer 200, and/or selecting the material of the substrate metal 210 are applicable for different types of filters 35, including layers 200 of different materials.

Now, therefore, the following is claimed:

1. An optical filtering system, comprising:
an optical filter having a layer composed of silicon formed on an opaque metal film substrate;
a light source for generating light, the light source positioned such that the light is incident on a surface of the layer, wherein the layer has an index of refraction and a thickness such that (1) a first portion of the light is reflected from the surface and (2) a second portion of the light at a wavelength corresponding to a second order optical resonance mode of the layer is absorbed by the layer thereby forming an absorption peak at the wavelength in the first portion of the light reflected from the surface, wherein the thickness of the layer is such that near perfect absorption of the light into the layer occurs at the wavelength, and wherein a first portion of the layer has a first thickness and a second portion of the layer has a second thickness different than the first thickness such that a second order optical resonance mode of the first portion of the layer is different than a second order optical resonance mode of the second portion of the layer; and
an optical detector positioned to detect the first portion of the light reflected from the surface.

2. An optical filter, comprising:
an opaque metal film substrate; and
a silicon film formed on the metal film substrate, wherein the silicon film has an index of refraction and a thickness such that (1) a first portion of light incident on the optical filter is reflected from a surface of the silicon film and (2) a second portion of the light at a wavelength corresponding to a second order optical resonance mode of the silicon film is absorbed by the silicon film thereby forming an absorption peak at the wavelength in the first portion of the light reflected from the surface, wherein the thickness of the layer is such that near perfect absorption of the light into the silicon film occurs at the wavelength, and wherein a first portion of the silicon film has a first thickness and a second portion of the silicon film has a second thickness different than the first thickness such that a second order optical resonance mode of the first portion of the silicon film is different than a second order optical resonance mode of the second portion of the silicon film.

3. The optical filter of claim 2, further comprising a dielectric layer formed on the metal film substrate between the silicon film and the metal film substrate.

4. The optical filter of claim 2, wherein the surface of the silicon film is flat.

5. The optical filter of claim 2, wherein the silicon film is capable of withstanding temperatures up to 500° Celsius.

6. The optical filter of claim 2, wherein the opaque metal film substrate comprises aluminum.

7. An optical filter method, comprising:
positioning an optical filter such that light is incident on and reflects from a surface of a silicon film of the optical filter, wherein the silicon film is formed on a metal film substrate; and
absorbing a portion of the light into the silicon film via a second order optical resonance mode of the silicon film such that the reflected light has an absorption peak, wherein a thickness of the silicon film is such that near perfect absorption of the portion of the light into the silicon film occurs at a peak absorption wavelength, and wherein a first portion of the silicon film has a first thickness and a second portion of the silicon film has a second thickness different than the first thickness such that a second order optical resonance mode of the first portion is different than a second order optical resonance mode of the second portion.

8. The method of claim 7, wherein the optical filter has a dielectric layer formed on the metal film substrate between the silicon film and the metal film substrate.

9. The method of claim 7, wherein the metal film substrate comprises aluminum.

10. A method, comprising:
providing an optical filter, wherein the providing comprises forming a silicon film on a metal film substrate;
identifying a wavelength of light to be absorbed by the optical filter;
selecting, based on the identifying, a thickness of the silicon film such that near perfect absorption of light into the silicon film is achieved at the wavelength for light incident on a surface of the silicon film such that a first portion of the light is reflected from the surface and a second portion of the light at the wavelength is absorbed into the silicon film thereby forming an absorption peak at the wavelength in the first portion reflected from the surface, wherein the forming is performed such that the silicon film has the selected thickness; and
thermally annealing the silicon film based on the identifying.

11. The method of claim 10, wherein the optical filter has a dielectric layer formed on the metal film substrate between the silicon film and the metal film substrate.

12. An optical filter, comprising:
an opaque metal film substrate; and
a silicon film formed on the metal film substrate, wherein the silicon film has an index of refraction and a thickness such that (1) a first portion of light incident on the optical filter is reflected from a surface of the silicon film and (2) a second portion of the light at a wavelength corresponding to a second order optical resonance mode of the silicon film is absorbed by the silicon film thereby forming an absorption peak at the wavelength in the first portion of the light reflected from the surface, wherein the thickness of the layer is such that near perfect absorption of the light into the silicon film occurs at the wavelength, and wherein a first portion of the metal film substrate is composed of a first metal and a second portion of the metal film substrate is composed of a second metal different than the first metal such that a second order optical resonance mode of a first portion of the silicon film formed on the first portion of the metal film substrate is different than a second order optical resonance mode of a second portion of the silicon film formed on the second portion of the metal film substrate.

13. An optical filter, comprising:
an opaque metal film substrate; and
a silicon film formed on the metal film substrate, wherein the silicon film has an index of refraction and a thickness such that (1) a first portion of light incident on the optical filter is reflected from a surface of the silicon film and (2) a second portion of the light at a wavelength corresponding to a second order optical resonance mode of the silicon film is absorbed by the silicon film thereby forming an absorption peak at the wavelength in the first portion of the light reflected from the surface, wherein the thickness of the layer is such that near perfect absorption of the light into the silicon film occurs at the wavelength, and wherein the surface of the silicon film is curved.

14. An optical filter method, comprising:
positioning an optical filter such that light is incident on and reflects from a surface of a silicon film of the optical filter, wherein the silicon film is formed on a metal film substrate; and
absorbing a portion of the light into the silicon film via a second order optical resonance mode of the silicon film such that the reflected light has an absorption peak, wherein a thickness of the silicon film is such that near perfect absorption of the portion of the light into the silicon film occurs at a peak absorption wavelength, and wherein a first portion of the metal film substrate is composed of a first metal and a second portion of the metal film substrate is composed of a second metal different than the first metal such that a second order optical resonance mode of a first portion of the silicon film formed on the first portion of the metal film substrate is different than a second order optical resonance mode of a second portion of the silicon film formed on the second portion of the metal film substrate.

15. A method, comprising:
providing an optical filter, wherein the providing comprises forming a silicon film on a metal film substrate, and wherein the metal film substrate has a first portion composed of a first metal and a second portion composed of a second metal different than the first metal;
identifying a wavelength of light to be absorbed by the optical filter; and
selecting, based on the identifying, a thickness of the silicon film such that near perfect absorption of light into the silicon film is achieved at the wavelength for light incident on a surface of the silicon film such that a first portion of the light is reflected from the surface and a second portion of the light at the wavelength is absorbed into the silicon film thereby forming an absorption peak at the wavelength in the first portion reflected from the surface, wherein the forming is performed such that the silicon film has the selected thickness.

16. A method, comprising:
providing an optical filter, wherein the providing comprises forming a silicon film on a metal film substrate;
identifying a wavelength of light to be absorbed by the optical filter; and
selecting, based on the identifying, a thickness of the silicon film such that near perfect absorption of light into the silicon film is achieved at the wavelength for light incident on a surface of the silicon film such that a first portion of the light is reflected from the surface and a second portion of the light at the wavelength is absorbed into the silicon film thereby forming an absorption peak at the wavelength in the first portion reflected from the surface, wherein the forming is performed such that the silicon film has the selected thickness, and wherein a first portion of the silicon film has a first thickness and a second portion of the silicon film has a second thickness different than the first thickness such that a second order optical resonance mode of the first portion of the silicon film is different than a second order optical resonance mode of the second portion of the silicon film.

17. A method, comprising:
providing an optical filter, wherein the providing comprises forming a silicon film on a metal film substrate;
identifying a wavelength of light to be absorbed by the optical filter; and
selecting, based on the identifying, a thickness of the silicon film such that near perfect absorption of light into the silicon film is achieved at the wavelength for light incident on a surface of the silicon film such that a first portion of the light is reflected from the surface and a second portion of the light at the wavelength is absorbed into the silicon film thereby forming an absorption peak at the wavelength in the first portion reflected from the surface, wherein the forming is performed such that the silicon film has the selected thickness, and wherein a first portion of the metal film substrate is composed of a first metal and a second portion of the metal film substrate is composed of a second metal different than the first metal such that a second order optical resonance mode of a first portion of the silicon film formed on the first portion of the metal film substrate is different than a second order optical resonance mode of a second portion of the silicon film formed on the second portion of the metal film substrate.

18. An optical filtering system, comprising:
an optical filter having a layer composed of silicon formed on an opaque metal film substrate;
a light source for generating light, the light source positioned such that the light is incident on a surface of the layer, wherein the layer has an index of refraction and a thickness such that (1) a first portion of the light is reflected from the surface and (2) a second portion of the light at a wavelength corresponding to a second order optical resonance mode of the layer is absorbed by the layer thereby forming an absorption peak at the wavelength in the first portion of the light reflected from the surface, wherein the thickness of the layer is such that near perfect absorption of the light into the layer occurs at the wavelength, and wherein the opaque metal film substrate comprises aluminum; and
an optical detector positioned to detect the first portion of the light reflected from the surface.

19. An optical filtering system, comprising:
an optical filter having a layer composed of silicon formed on an opaque metal film substrate;
a light source for generating light, the light source positioned such that the light is incident on a surface of the layer, wherein the layer has an index of refraction and a thickness such that (1) a first portion of the light is reflected from the surface and (2) a second portion of the light at a wavelength corresponding to a second order optical resonance mode of the layer is absorbed by the layer thereby forming an absorption peak at the wavelength in the first portion of the light reflected from the surface, wherein the thickness of the layer is such that near perfect absorption of the light into the layer occurs at the wavelength, and wherein the metal film substrate comprises aluminum; and
an optical detector positioned to detect the first portion of the light reflected from the surface.

20. An optical filtering system, comprising:
an optical filter having a layer composed of silicon formed on an opaque metal film substrate;
a light source for generating light, the light source positioned such that the light is incident on a surface of the layer, wherein the layer has an index of refraction and a thickness such that (1) a first portion of the light is reflected from the surface and (2) a second portion of the light at a wavelength corresponding to a second order optical resonance mode of the layer is absorbed by the layer thereby forming an absorption peak at the wavelength in the first portion of the light reflected from the surface, wherein the thickness of the layer is such that near perfect absorption of the light into the layer occurs at the wavelength, and wherein a first portion of the opaque metal film substrate is composed of a first metal and a second portion of the opaque metal film substrate is composed of a second metal different than the first metal such that a second order optical resonance mode of a first portion of the silicon film formed on the first portion of the opaque metal film substrate is different than a second order optical resonance mode of a second portion of the silicon film formed on the second portion of the opaque metal film substrate; and
an optical detector positioned to detect the first portion of the light reflected from the surface.

21. An optical filtering system, comprising:
an optical filter having a layer composed of silicon formed on an opaque metal film substrate;
a light source for generating light, the light source positioned such that the light is incident on a surface of the layer, wherein the layer has an index of refraction and a thickness such that (1) a first portion of the light is reflected from the surface and (2) a second portion of the light at a wavelength corresponding to a second order optical resonance mode of the layer is absorbed by the layer thereby forming an absorption peak at the wavelength in the first portion of the light reflected from the surface, wherein the thickness of the layer is such that near perfect absorption of the light into the layer occurs at the wavelength, and wherein the surface of the layer is curved; and
an optical detector positioned to detect the first portion of the light reflected from the surface.

* * * * *